(12) United States Patent
Bharat et al.

(10) Patent No.: US 10,265,544 B2
(45) Date of Patent: Apr. 23, 2019

(54) REAL-TIME TUMOR PERFUSION IMAGING DURING RADIATION THERAPY DELIVERY

(71) Applicant: KONINKLIJKE PHILIPS N.V., Eindhoven (NL)

(72) Inventors: Shyam Bharat, Cortlandt Manor, NY (US); Christopher Stephen Hall, Kirkland, WA (US)

(73) Assignee: Koninklijke Philips N.V., Eindhoven (NL)

( * ) Notice: Subject to any disclaimer, the term of this patent is extended or adjusted under 35 U.S.C. 154(b) by 50 days.

(21) Appl. No.: 14/411,115

(22) PCT Filed: Jun. 18, 2013

(86) PCT No.: PCT/IB2013/054986
§ 371 (c)(1),
(2) Date: Dec. 24, 2014

(87) PCT Pub. No.: WO2014/001961
PCT Pub. Date: Jan. 3, 2014

(65) Prior Publication Data
US 2015/0165234 A1   Jun. 18, 2015

Related U.S. Application Data

(60) Provisional application No. 61/665,979, filed on Jun. 29, 2012.

(51) Int. Cl.
*A61B 5/00* (2006.01)
*A61N 5/10* (2006.01)
(Continued)

(52) U.S. Cl.
CPC .......... *A61N 5/1039* (2013.01); *A61B 5/0095* (2013.01); *A61B 5/0261* (2013.01);
(Continued)

(58) Field of Classification Search
CPC ....... A61B 5/0515; A61B 5/055; A61B 5/415; A61B 5/418; A61B 5/4504
See application file for complete search history.

(56) References Cited

U.S. PATENT DOCUMENTS 7,343,030 B2 * 3/2008 Sawyer ............... A61N 5/1049
378/65
8,160,205 B2   4/2012 Saracen et al.
(Continued)

FOREIGN PATENT DOCUMENTS

CN   1110120 A   10/1995
EP   2407927 A1   1/2012
(Continued)

OTHER PUBLICATIONS

Peter Schmitt et al; "Quantitative Tissue Perfusion Measurements in Head and Neck Carcinoma Patients Before and During Radiation Therapy With a Non-Invasive MR Imaging Spin-Labeling Technique", Radiotherapy and Oncology, vol. 67, No. 1, Apr. 1, 2003, pp. 27-34, XP055087827.
(Continued)

*Primary Examiner* — Joel Lamprecht (57) ABSTRACT

A system and method for perfusion imaging includes an imaging device (122) configured to collect perfusion information from a target area. A processing module (110) is configured to determine perfusion levels of the target area based on the perfusion information. A planning module (114) is configured to provide a treatment plan for the target area by correlating the perfusion levels with treatment activities for the target area, wherein the treatment activities are adjusted based upon characteristics of the perfusion levels in the target area.

19 Claims, 4 Drawing Sheets

(51) Int. Cl.
*A61B 5/1455* (2006.01)
*A61B 5/026* (2006.01)
*A61B 8/08* (2006.01)
*A61B 34/30* (2016.01)
*A61B 5/145* (2006.01)

(52) U.S. Cl.
CPC ........ *A61B 5/14551* (2013.01); *A61B 5/4836* (2013.01); *A61B 5/4839* (2013.01); *A61B 8/085* (2013.01); *A61B 34/30* (2016.02); *A61N 5/1064* (2013.01); *A61N 5/1077* (2013.01); *A61B 5/0059* (2013.01); *A61B 5/14542* (2013.01); *A61B 5/4848* (2013.01); *A61B 2576/00* (2013.01)

(56) References Cited

U.S. PATENT DOCUMENTS

| | | | |
|---|---|---|---|
| 2003/0060693 | A1 | 3/2003 | Monfre et al. |
| 2003/0211036 | A1 | 11/2003 | Degani et al. |
| 2005/0234327 | A1 | 10/2005 | Saracen et al. |
| 2009/0256078 | A1 | 10/2009 | Mazin |
| 2011/0257561 | A1* | 10/2011 | Gertner ............ A61B 5/412 601/2 |
| 2012/0003160 | A1 | 1/2012 | Wolf et al. |
| 2012/0035462 | A1* | 2/2012 | Maurer, Jr. .......... A61B 8/4245 600/411 |
| 2012/0052010 | A1* | 3/2012 | Sorensen ........... A61K 51/0402 424/1.89 |
| 2012/0063665 | A1 | 3/2012 | Wang et al. |
| 2013/0037722 | A1 | 2/2013 | Yamaya |

FOREIGN PATENT DOCUMENTS

| | | |
|---|---|---|
| JP | 2000105279 A | 4/2000 |
| JP | 2001231769 A | 8/2001 |
| JP | 2004097646 A | 4/2004 |
| JP | 2011514213 A | 5/2011 |
| JP | 2012506734 A | 3/2012 |
| WO | 2008029407 A2 | 3/2008 |
| WO | 2010044879 A2 | 4/2010 |
| WO | 2011121737 A1 | 10/2011 |
| WO | 2011127428 A2 | 10/2011 |
| WO | 2012048295 A2 | 4/2012 |
| WO | 2012080948 A1 | 6/2012 |

OTHER PUBLICATIONS

Sidi, R., "An alternative to radioactive microspheres for measuring regional myocardial blood glow, part 2: Laser-doppler perfusion monitor", Journal of Cardiothoracic and Vascular Anesthesia, Apr. 1, 1996, Philadelphia, PA, vol. 10, No. 3, p. 374-377.
Japan Patent Office. Report of Reconsideration, dated Dec. 26, 2018, application No. JP 20150519408 (JP counterpart of sn 14/411115). no. English translation is available.

* cited by examiner

REAL-TIME TUMOR PERFUSION IMAGING DURING RADIATION THERAPY DELIVERY

This application is a national stage application under 35 U.S.C. § 371 of International Application No. PCT/IB2013/054986 filed on Jun. 18, 2013 and published in the English language on Jan. 3, 2014 as International Publication No. WO 2014/001961 A1, which claims priority to U.S. Application No. 61/665,979 filed on Jun. 29, 2012, the entire disclosures of which are incorporated herein by reference.

This disclosure relates to medical instruments and more particularly to tumor perfusion imaging during radiation therapy delivery.

Radiation therapy (RT) is commonly used for the treatment of cancer. Conventionally, RT treatment plans have been static in that they are created and delivered without any modification between fractions. RT used in conjunction with chemotherapy enhances the treatment of cancer, as the uptake of the chemotherapeutic agent by the tumor increases the effectiveness of RT. The uptake of the chemotherapeutic agent by the tumor is determined by the concentration levels of the agent in the tumor, which in turn is dependent on tumor perfusion levels. Thus, the ability to measure changes in tumor perfusion during RT delivery may yield valuable feedback in determining adaptations to the RT treatment plan for the remaining fractions and also in determining the appropriate drug delivery patterns for administering chemotherapy. However, there are currently no methods for non-invasively quantifying tumor response in real-time during RT delivery.

In accordance with the present principles, a imaging system includes an imaging device configured to collect perfusion information from a target area. A processing module is configured to determine perfusion levels of the target area based on the perfusion information. A planning module is configured to provide a treatment plan for the target area by correlating the perfusion levels with treatment activities for the target area, wherein the treatment activities are adjusted based upon characteristics of the perfusion levels in the target area.

A perfusion imaging system includes an imaging device configured to collect perfusion information from a target area. A processing module is configured to determine perfusion levels of the target area based on the perfusion information. A planning module configured to provide a treatment plan for the target area by correlating the perfusion levels with treatment activities for the target area, wherein the treatment activities are adjusted based upon characteristics of the perfusion levels in the target area by using at least one of tumor perfusion levels and normal tissue perfusion levels as optimization parameters. The treatment activities include at least one of radiation therapy and chemotherapy.

A method for perfusion imaging includes collecting perfusion information from a target area. Perfusion levels of the target area are determined based on the perfusion information. A treatment plan for the target area is provided by correlating the perfusion levels with treatment activities for the target area, wherein the treatment activities are adjusted based upon characteristics of the perfusion levels in the target area.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, systems and methods for perfusion imaging are provided. A result of ionizing radiation and chemotherapy is a change in the levels of hemoglobin and water content in irradiated tissue regions, as well as a change in local perfusion patterns with increased vasodilation. Perfusion imaging techniques measure tissue concentration of hemoglobin, water, oxygen saturation and flow to obtain perfusion levels of a tumor during radiation therapy delivery as a measure of the radiation therapy's effectiveness. Perfusion levels may be obtained in real-time or intermittently between radiation therapy fractions.

Preferably, a probe of a perfusion imaging device is positioned such that it does not interfere with an active radiation therapy beam. In one embodiment, the probe is coupled to a robotic arm to position the probe. The probe may be positioned based on one or more of the following: a currently active RT beam; a signal-to-noise ratio of the optical signal; the known temporal pattern of linac positions obtained from the RT planning system and/or the record and verify system; and an exit path of each active beam. Alternatively, the probe may be positioned based upon an output of the RT planning system of the optimal static location for monitoring the largest field of view during the procedure.

In a particularly useful embodiment, perfusion levels of a target area are correlated with treatment activities to provide a treatment plan for the target area. Preferably, the treatment activities may be adjusted based upon characteristics of the perfusion levels in the target area. Treatment activities may include radiation therapy. For example, tumor perfusion levels and normal (i.e., healthy) tissue perfusion levels may be utilized as optimization parameters in radiation therapy planning. Treatment activities may also include chemotherapy treatment that is administered alongside radiation therapy.

Advantageously, the present principles determine perfusion levels of a tumor in a safe and non-invasive manner. By measuring changes in tumor perfusion during radiation therapy delivery, important information can be garnered regarding the response of different tumor types and cancer stages to radiation therapy. This data may be utilized to tailor radiation therapy treatment plans or chemotherapy treatment plans to specific types and locations of tumors.

It should be understood that the present invention will be described in terms of medical imaging instruments; however, the teachings of the present invention are much broader and are applicable to any imaging instrument. In some embodiments, the present principles are employed in analyzing or treating complex biological or mechanical systems. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
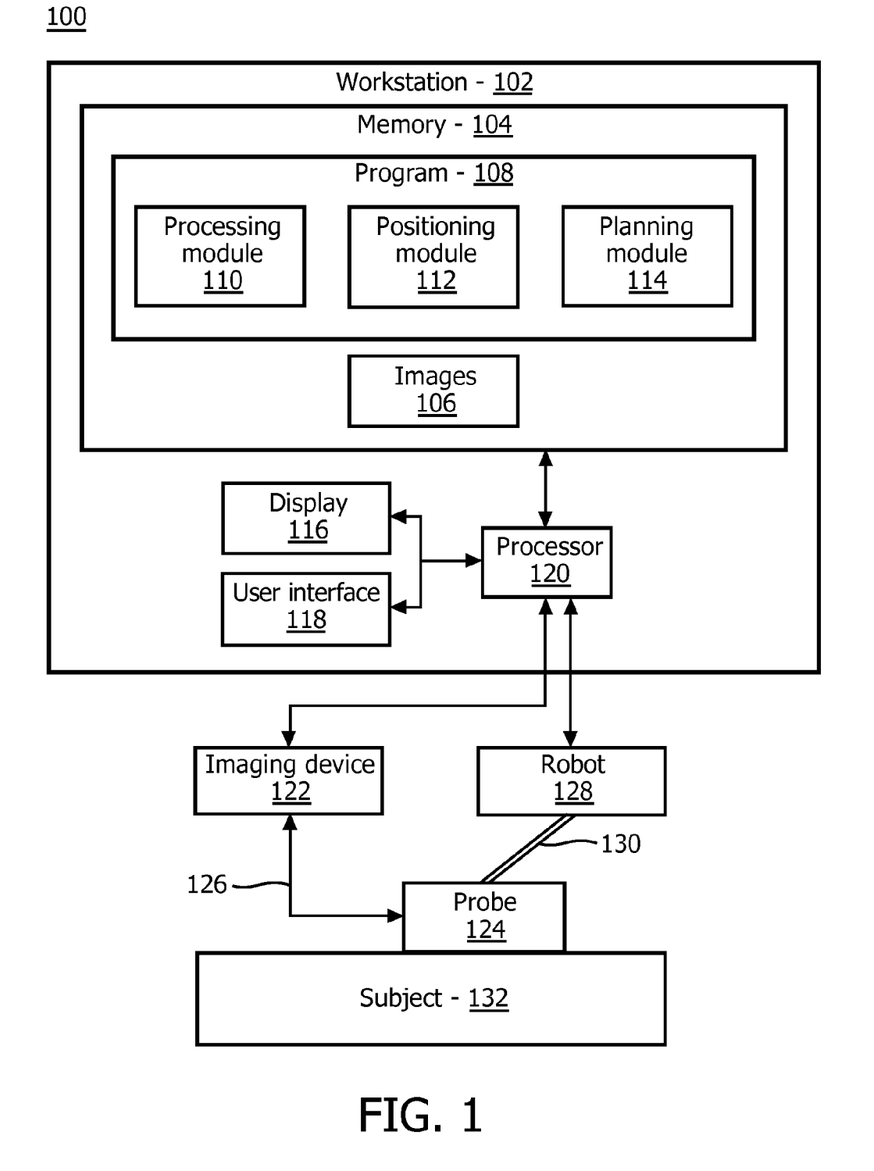
FIG. 1 is a block/flow diagram showing a perfusion imaging system in accordance with one illustrative embodiment.

Referring now to the drawings in which like numerals represent the same or similar elements and initially to FIG. 1, a system 100 for perfusion imaging is illustratively shown in accordance with one embodiment. Ionizing radiation and chemotherapy change levels of hemoglobin and water content in the irradiated tissue regions, as well as local perfusion patterns with increased vasodilation. Tissue regions with increased perfusion levels are more radiosensitive. Thus, system 100 may monitor tumor perfusion levels to garner important information regarding the quantitative response of different tumor types and cancer stages to radiation therapy (RT).

While the present principles are preferably applied for the real-time monitoring of tumor perfusion during RT delivery, it is noted that the teachings of the present principles are not limited to the monitoring of tumor perfusion or the treatment of cancer, but rather are much broader and may be applied in various fields for a number of different applications. For example, in one embodiment, the present principles may be applied in plumbing to detect perfusion in pipes to be repaired. Other applications are also contemplated within the scope of the present principles.

The system 100 may include a workstation or console 102 from which procedures (e.g., RT and chemotherapy) are supervised and managed. Workstation 102 preferably includes one or more processors 120 and memory 104 for storing programs and applications. Memory 104 may also store data 106, such as perfusion images derived from one or more imaging devices 122 and probes 124. It should be understood that the functions and components of system 100 may be integrated into one or more workstations or systems.

Workstation 102 may include one or more displays 116 for viewing data 106. The display 116 may also permit a user to interact with the workstation 102 and its components and functions. This is further facilitated by a user interface 118, which may include a keyboard, mouse, joystick, or any other peripheral or control to permit user interaction with workstation 102.

The probe 124 and imaging device 122 may include any device sensitive to changes in perfusion patterns. It is noted that the term perfusion, as used herein, includes blood flow, oxygen saturation, scattering properties of tissue, exogenous contrast uptake in the tissue, and similar physiological measures. The probe 124 of the imaging device 122 may collect perfusion information from a target area. Preferably, the target area includes a tumor and healthy tissue. In other embodiments, for example, where both the tumor and healthy tissue are unable to be evaluated within a target area, two separate target areas may be evaluated, where the first target area evaluates the tumor and the second target area evaluates the healthy tissue. In particularly useful embodiments, imaging device 122 may be configured to perform, for example, one or more of the following: diffuse optical spectroscopy (DOS), diffuse optical imaging (DOI), diffuse correlation spectroscopy (DCS), photoacoustic computed tomography (PAT), photoacoustic microscopy (PAM), laser doppler perfusion imaging (LDPI), polarization sensitive optical coherence tomography (PSOCT), high frequency ultrasound (US), etc. It is noted that the above-identified functions of imaging device 122 are illustrative and not meant to be limiting. Other functions and configurations of imaging device 122 are also contemplated. In one embodiment, one or more probes 124 are coupled to the imaging device 122 through cabling 126 to evaluate a subject 132 (e.g., a patient). The cabling 126 may include electrical connections, optical fiber connections, instrumentation, etc., as needed. In other embodiments, probe 124 may be coupled to imaging device 122 via a wireless link (e.g., radio frequency communication, Wi-Fi™, Bluetooth™, etc.).

In an embodiment, the imaging device 122 is configured to perform DOS. DOS is an optical technique utilizing light in the near-infrared (NIR) spectral range to quantitatively measure absorption and scattering. Absorption spectra are used by processing module 110 to calculate the tissue concentration of oxygenated and deoxygenated hemoglobin, water and bulk lipids. Advantageously, DOS does not need exogenous contrast and provides rapid quantitative and functional information (e.g., imaging updates every 10 seconds). DOS employs a large spectral bandwidth, but has a low spatial sampling rate.

In another embodiment, the imaging device 122 is configured to perform DOI. DOI is a complementary tool that provides a large spatial sampling rate, but with a low spectral bandwidth. Thus, DOI may be tuned to provide absorption characteristics of specific chromophores (e.g., hemoglobin, water, etc.). A probe 122 of imaging device 120 configured to perform DOI may include optical fibers for illumination and detection. For illumination, the optical fibers may be connected to, e.g., a laser diode source or light emitting diode (LED). For detection, the optical fibers may be connected to, e.g., an intensified charge-coupled device (CCD) camera detector or photodetector. Simultaneous illumination and detection may be carried out using different optical fibers. For example, the probe 122 may utilize continuous wave (CW) optical measurements to generate real-time 2D images of tumor perfusion levels. Other measures of perfusion levels are also contemplated, such as frequency domain (FD) measurements and time domain (TD) measurements. The imaging device 120 configured to perform DOI may be tuned to image at a range of variable depths in the tissue by adjusting the source-detector configuration.

Figure 2:
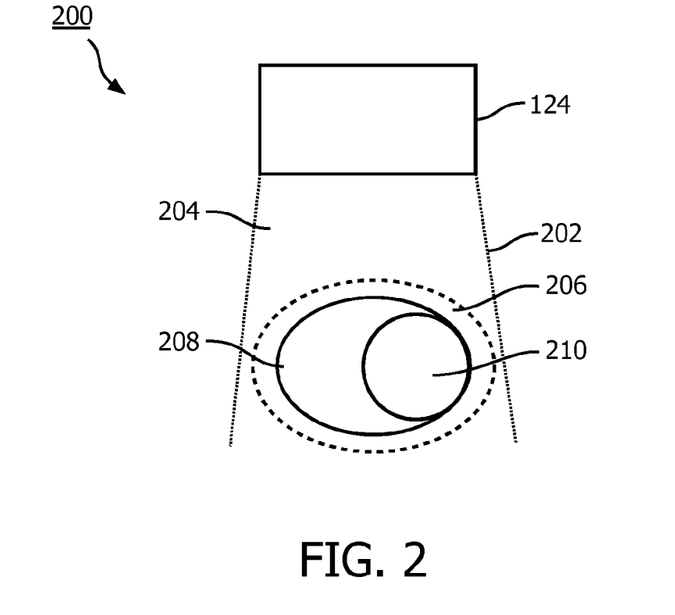
FIG. 2 shows a perfusion imaging system applied to monitor perfusion levels of a tumor in accordance with one illustrative embodiment.

Referring for a moment to FIG. 2, with continued reference to FIG. 1, a perfusion imaging system applied to monitor perfusion levels of a tumor 200 is illustratively depicted in accordance with one embodiment. A probe 124 of an imaging device 122 (FIG. 1) measures perfusion levels of normal tissue 202 and partial tumor volume 206 within imaging plane 204. Measured perfusion levels may be particularly useful where a partial tumor volume 210 responds differently to RT than the rest of the tumor 208.

Figure 3:
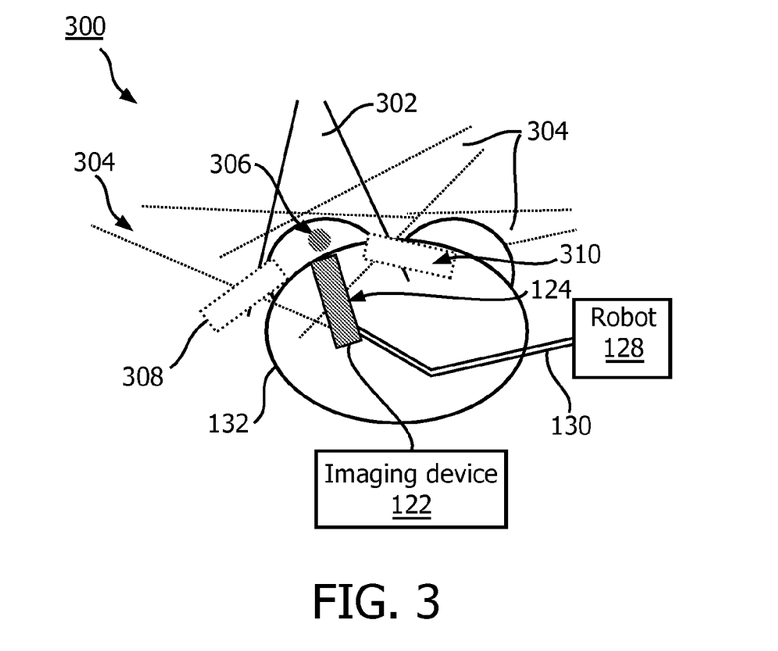
FIG. 3 shows a cross sectional view of a subject with a perfusion imaging system applied to image a tumor on a breast in accordance with one illustrative embodiment.

Referring back to FIG. 1, in one embodiment, the system 100 includes a robot 128 with a robotic arm 130 coupled to the probe 124. Preferably, the robotic arm 130 includes multiple degrees of freedom to position the probe 124 so as to not interfere with an active (e.g., RT radiation) beam. Referring for a moment to FIG. 3, with continued reference to FIG. 1, a cross sectional view of a subject with a perfusion imaging system applied to image perfusion levels of a tumor on a breast during RT delivery 300 is illustratively depicted in accordance with one embodiment. A probe 124 of imaging device 122 is positioned to image perfusion levels of a tumor 306 using a robotic arm 130 of robot 128 so as to not interfere with the path of an active radiation beam 302 during RT delivery. For example, the probe 122 may be positioned in the exit path of a currently active radiation beam 302 so that the tumor is optically visible at all times. As the inactive radiation beams 304 are activated, the probe 124 may be repositioned to alternate locations 308, 310.

Referring back to FIG. 1, a computer implemented program 108 is stored in memory 104 of workstation 102. The program 108 may include a number of modules, each configured to perform various functions. It should be understood that the modules may be implemented in various combinations of hardware and software.

The program 108 may include processing module 110, which is configured to receive data from imaging device 122 to determine perfusions levels of the target area based on the perfusion information. The perfusions levels may indicate a quantifiable measurement of the amount of hemoglobin and water in a tumor at any instant and may provide indications of its propensity for radiation-induced cell death. On the other hand, normal (i.e., non-cancerous) tissue is less radiosensitive than cancerous tissue. Hence, monitoring perfusion levels of surrounding normal tissue during RT delivery may provide evolving information of its changing radiosensitivity due to the incidental radiation received by the normal tissue.

In a particularly useful embodiment, processing module 110 determines perfusion levels using the perfusion index (PI). PI is a measure of pulse strength of a NIR signal reflected from the tumor or tissue. The amplitude of light detected at various positions along tissue surfaces provides information about the absorption and scattering of the underlying tissue. Specifically, the concentration of oxygenated and deoxygenated hemoglobin can be derived by using multiple wavelengths of light in the NIR range. The concentrations of the optically absorbing chromophores can be used as a measure of the tumor microenvironment, allowing for better understanding of tumor perfusion, necrosis, and angiogenesis. Other measures of perfusion levels are also contemplated. For example, exogenous contrast agents may be used to differentiate well-perfused tissue from poorly-perfused tissue, to identify cell death in the tumor region, or to identify the tumor itself.

The processing module 110 may generate two-dimensional (2D) and/or three-dimensional (3D) images of spatial patterns in tissue as an output. In one embodiment, where the imaging device 122 is configured to perform diffuse optical imaging, images may be reconstructed based on the radiative transport equation to model light propagation in tissue. In other embodiment, images of diffuse optical imaging may be reconstructed using the diffusion approximation to the radiative transport equation. Other methods of generating perfusion images are also contemplated. In one embodiment, the processing module 110 may be configured to measure tumor perfusion during RT delivery in real-time. In another embodiment, the processing module 110 may be configured to measure tumor perfusion intermittently after a subset of one or more fractions of RT. The processing module 110 may also provide chromophore concentrations as a measure of tumor response and/or normal tissue response as an output. The output may involve one or more displays 116 and user interfaces 118. In one embodiment, one display 116 may show the values of tumor/normal tissue response updated in real-time, while another display 116 may show cumulative values of tissue response to the RT delivery. Other configurations are also contemplated.

In an embodiment, the program 108 may include a positioning module 112 to position the probe 124 using a robotic arm 130 of robot 128 so as to not interfere with the path of an active radiation beam. The positioning module 112 may control the position of probe 124 based on one or more of the following: the position of the active RT beam; the signal-to-noise ratio of the optical signal; known temporal pattern of linac positions obtained from the RT planning system and/or the record and verify (R&V) system; and the exit path of the active RT beam. In another embodiment, the positioning module 112 receives an optimal static location from an RT planning system for monitoring the largest field of view during the procedure. Other positioning factors are also contemplated.

The program 108 may include a planning module 114. In one embodiment, the planning module 114 may provide a treatment plan for the target area by correlating the perfusion levels with treatment activities for the target area. Treatment activities may include radiation therapy, chemotherapy, etc. Other treatment activities are also contemplated. The treatment activities may be adjusted based upon characteristics of the perfusion levels in the target area. For example, the planning module 114 may incorporate the tumor response as an optimization parameter in the dose optimization procedure of RT. As another example, the planning module 114 may incorporate the normal tissue response as an optimization parameter in the dose optimization procedure of RT. In other embodiments, the optimization parameters may include perfusion levels of normal tissue and/or tumors may be combined with other physiological measures, such as, e.g., oxygen saturation, scattering properties of tissue, exogenous contrast uptake in the tissue, etc. The planning module 114 may adapt remaining fractions of RT delivery by creating optimized RT plans, with the tumor response and/or the normal tissue response as additional optimization parameters.

The perfusion levels in the tumor should ideally be high during the first few fractions of RT, meaning that the tumor continues to be radiosensitive. As the percentage of cell death in the tumor increases towards the later fractions of RT, there should be little to no perfusion in those regions. On the other hand, in normal tissue, higher perfusion levels indicate increased radiosensitivity, which may point to an increased need to avoid those regions in the RT plan. Another embodiment may include altering the intra-fraction delivery through active measurement of perfusion levels and locally altering the dosage to those sites. These features may be particularly useful in cases where the tumor is located close to sensitive structures (e.g., spinal cord), where it is important to maintain physiological function after the RT procedure. These features may also be useful where part of the tumor responds differently to treatment than the remaining regions of the tumor.

In another embodiment, the planning module 114 may utilize tumor perfusion levels for intelligent planning strategies with respect to combination therapies. For example, when chemotherapy is utilized in conjunction with RT, the uptake of the chemotherapeutic agent by the tumor also serves to make the tumor more radiosensitive. It may be important to utilize the measured tumor perfusion levels at all stages during therapy to continuously adapt the remaining portion of the therapy course. This adaptation may be applicable to the treatment patterns of both RT and chemotherapy.

Figure 4:
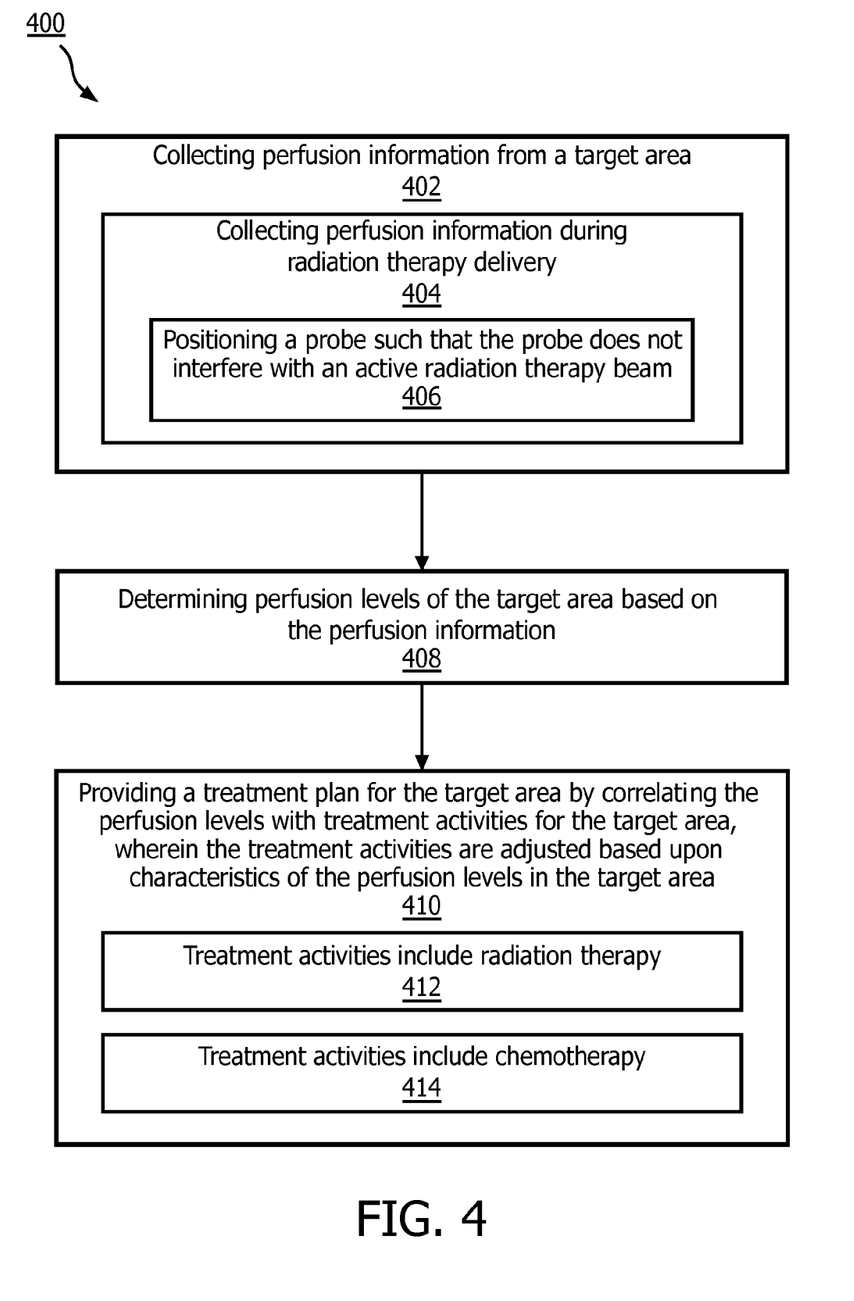
FIG. 4 is a block/flow diagram showing a method for perfusion imaging in accordance with one illustrative embodiment.

Referring now to FIG. 4, a flow diagram showing a method for perfusion imaging 400 is illustratively depicted in accordance with one embodiment. In block 402, perfusion information is collected from a target area. In a preferred embodiment, the target area includes both a tumor and healthy tissue. In other embodiments, for example, where both the tumor and healthy tissue are unable to be evaluated within a target area, two separate target areas may be evaluated, with the first target area evaluating the tumor and the second target area evaluating healthy tissue. Collecting perfusion information includes applying any method to identify changes in local perfusion patterns. It should be understood that the term perfusion used herein is meant to include blood flow, oxygen saturation, scattering properties of tissue, exogenous contrast uptake in the tissue, and similar physiological measures. In some useful embodiments, collecting perfusion information includes, for example, performing one or more of the following: diffuse optical spectroscopy, diffuse optical imaging, diffuse correlation spectroscopy, photoacoustic computed tomography, photoacoustic microscopy, laser doppler perfusion imaging, polarization sensitive optical coherence tomography, high frequency ultrasound, etc. Other methods of collecting perfusion information are also contemplated.

In block 404, collecting perfusion information may be performed during radiation therapy treatment. In block 406, a probe of an imaging device configured to collect perfusion information is positioned such that the probe does not interfere with an active radiation therapy beam. The probe may be positioned based on at least one of the following: a currently active RT beam; a signal-to-noise ratio of the optical signal; the known temporal pattern of linac positions obtained from the RT planning system and/or the record and verify system; and an exit path of each active beam. Alternatively, the probe may be positioned based upon an output of the RT planning system of the optimal static location for monitoring the largest field of view during the procedure. Other methods of positioning the probe of the perfusion imaging device are also contemplated. In a particularly useful embodiment, the probe is coupled to a robot by a robotic arm to position the probe. Preferably, the robotic arm includes multiple degrees of freedom.

In block 408, perfusion levels of the target area are determined using the perfusion information. Determining perfusion levels may include generating 2D and/or 3D images of spatial patterns of the target area of tissue. In one embodiment, perfusion levels may also be provided intermittently after a subset of one or more fractions of RT. In another embodiment, perfusion levels may further be provided as cumulative values of tissue response to RT delivery. In still another embodiment, perfusion levels may be provided in combination with other physiological measures that may be obtained through imaging, such as oxygen saturation, scattering properties of the tissue, exogenous contrast uptake in the tissue, etc.

In block 410, a treatment plan for the target area is provided by correlating the perfusion levels with treatment activities for the target area. Treatment activities may include, e.g., radiation therapy, chemotherapy, etc. Other treatment activities are also contemplated. Preferably, treatment activities may be adjusted based upon characteristics of the perfusion levels in the target area. In block 412, adjusting treatment activities includes adjusting radiation therapy. Remaining treatment fractions of RT may be adapted using the tumor perfusion levels and/or the normal tissue perfusion levels as additional optimization parameters in RT planning. The tumor perfusion levels and the normal tissue perfusion levels may be applied as optimization parameters in RT planning alone or in combination with each other or other physiological measures, such as oxygen saturation, scattering properties of the tissue, exogenous contrast uptake in the tissue, etc. For instance, in initial fractions of RT, perfusion levels in the tumor should be high, which means that the tumor continues to be radiosensitive. As the percentage of cell death increases towards later fractions of RT, there should be little to no perfusion in those regions. In normal tissue, higher perfusion levels indicate increased radiosensitivity, which may point to an increased need to avoid those regions in RT planning. In another embodiment, intra-fraction delivery may be adapted through active measurement of perfusion levels and locally altering the dosage to those sites. Adapting RT treatment may be particularly useful where the tumor is located close to sensitive structures (e.g., spinal cord), where it is important to maintain physiological function after the RT procedure.

In block 414, adjusting treatment activities includes adjusting chemotherapy treatment. For example, chemotherapy may be applied alongisde RT. The uptake of the chemotherapeutic agent by the tumor makes the tumor more radiosensitive. In these situations, it is important to utilize the measured tumor perfusion levels at all stages of therapy to continuously adapt the remaining portions of the therapy. The adaption may be applicable to the treatment planning of RT and/or chemotherapy.

Figure 5:
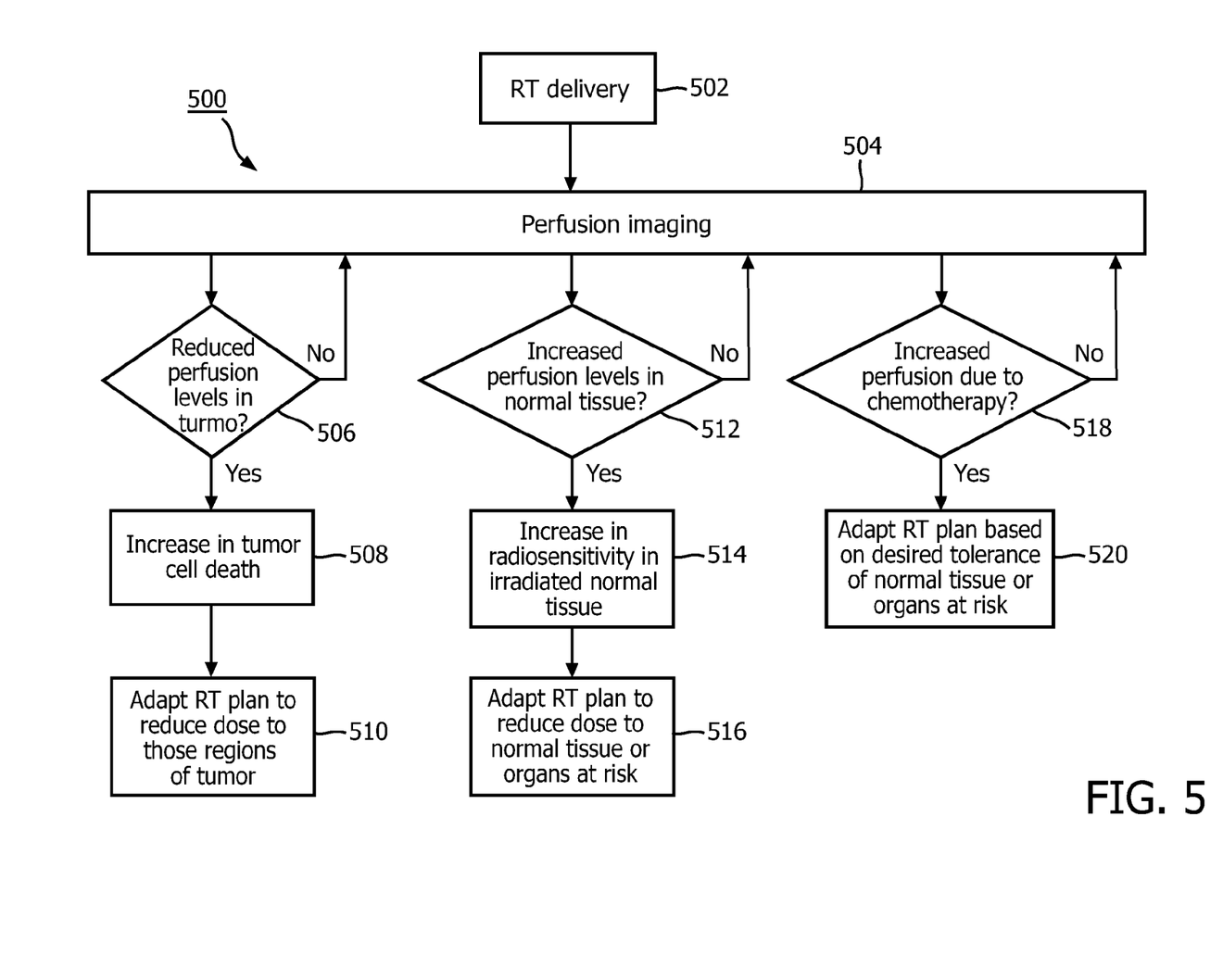
FIG. 5 is a block/flow diagram showing exemplary use cases utilizing perfusion levels to adapt therapy in accordance with one illustrative embodiment.

Referring for a moment to FIG. 5, an exemplary flow diagram 500 of use cases utilizing perfusion levels to adapt therapy is illustratively depicted. In block 502, radiation therapy delivery is performed on a target area, preferably including a tumor and healthy tissue. In block 504, perfusion imaging is performed. Perfusion imaging may be performed inter-fractionally or intra-fractionally. Perfusion imaging may include, for example, DOS, DOI, etc. In block 506, if there is a reduction in perfusion levels in the tumor, this may indicate an increase in tumor cell death in block 508. In block 510, the radiation therapy treatment plan may be adapted to reduce the dosage to those regions of the tumor. In block 512, if there is an increase in perfusion levels in the normal tissue, this may indicate that the irradiated normal tissue is becoming more radiosensitive in block 514. In block 516, the radiation therapy treatment plan may be adapted to reduce the dosage to the normal tissue or the organs at risk. In block 518, if there is an increase in perfusion levels due to chemotherapy, in block 520, the radiation therapy treatment plan may be adapted (e.g., dose, fractionation, etc.) based on the desired tolerance of the normal tissue or the organs at risk.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for real-time tumor perfusion imaging during radiation therapy delivery (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A perfusion imaging system, comprising:
an imaging device configured to collect perfusion information from a target area at predetermined intervals during treatment activities,
wherein the treatment activities include fractionated radiation therapy;
one or more processors configured to determine perfusion levels of the target area based on the perfusion information and further configured to provide a treatment plan for the target area by correlating the perfusion levels with treatment activities for the target area, wherein the radiation therapy administered during a fraction of the fractionated radiation therapy is adjusted intra-fractionally in response to the perfusion information collected from the target area during the fraction.

2. The system as recited in claim 1, wherein the treatment activities are adjusted by using at least one of tumor perfusion levels or normal tissue perfusion levels as optimization parameters.

3. The system as recited in claim 2, wherein the treatment activities are adjusted by using the at least one of tumor perfusion levels or normal tissue perfusion levels in combination with one or more physiological measures as optimization parameters.

4. The system as recited in claim 1, wherein the treatment activities include chemotherapy to be administered alongside radiation therapy.

5. The system as recited in claim 1, wherein the one or more processors is further configured to position a probe of the imaging device such that it does not interfere with an active radiation therapy radiation beam.

6. The system as recited in claim 5, wherein the one or more processors is further configured to position the probe based on at least one of: the active radiation therapy radiation beam, a signal-to-noise ratio of the response of the probe, a known temporal pattern of linac position, or an exit path of the active radiation therapy radiation beams.

7. The system as recited in claim 5, wherein the one or more processors is further configured to position the probe according to a location received from a radiation therapy planning system for monitoring a largest field of view.

8. The system as recited in claim 1, further comprising a robotic arm coupled to a probe of the imaging device to position the probe.

9. The system as recited in claim 8, wherein the robotic arm includes two or more degrees of freedom.

10. The system as recited in claim 1, wherein the imaging device collects perfusion information during radiation therapy delivery.

11. The system as recited in claim 10, wherein the one or more processors is further configured to determine perfusion levels after a set of one or more radiation therapy fractions.

12. The system as recited in claim 10, wherein the one or more processors is further configured to determine a cumulative perfusion level.

13. The system as recited in claim 1, wherein the one or more processors is further configured to determine perfusion levels in real-time during radiation therapy delivery.

14. The system as recited in claim 1, wherein the imaging device is of at least one of the following modalities: diffuse optical spectroscopy, diffuse optical imaging, diffuse correlation spectroscopy, photoacoustic computed tomography, photoacoustic microscopy, laser doppler perfusion imaging, polarization sensitive optical coherence tomography, or high frequency ultrasound.

15. A perfusion imaging system, comprising:
a processing module configured to determine perfusion levels of a target area based on perfusion information collected from the target area at predetermined intervals during treatment activities by an imaging device, wherein the treatment activities include fractionated radiation therapy; and
a planning module configured to provide a treatment plan for the target area by correlating the perfusion levels with the treatment activities for the target area, wherein the radiation therapy administered during a fraction of the fractionated radiation therapy is adjusted intra-fractionally in response to the perfusion levels in the target area determined during the fraction by using at least one of tumor perfusion levels or normal tissue perfusion levels as optimization parameters.

16. The system as recited in claim 15, further comprising a positioning module configured to position a probe of the imaging device such that it does not interfere with an active radiation therapy radiation beam.

17. The system as recited in claim 15, wherein a robotic arm having two or more degrees of freedom is coupled to a probe to position the probe.

18. A method for perfusion imaging, comprising:
    collecting perfusion information from a target area at predetermined intervals during treatment activities, wherein the treatment activities include fractionated radiation therapy;
    determining perfusion levels of the target area based on the perfusion information; and
    using one or more processors ot calculate and provide a treatment plan for the target area by correlating the perfusion levels with the treatment activities for the target area, wherein the radiation therapy administered during a fraction of the fractionated radiation therapy is adjusted intra-fractionally in response to the perfusion levels in the target area determined during the fraction.

19. The method as recited in claim 18, wherein the treatment activities are adjusted by using at least one of tumor perfusion levels or normal tissue perfusion levels as optimization parameters; and wherein the treatment activities are adjusted by using the at least one of tumor perfusion levels or normal tissue perfusion levels in combination with one or more physiological measures as optimization parameters.

* * * * *